United States Patent
Peyman

(12) 
(10) Patent No.: US 6,264,648 B1
(45) Date of Patent: *Jul. 24, 2001

(54) CORNEAL CURVATURE MODIFICATION VIA INTERNAL ABLATION

(75) Inventor: Gholam A. Peyman, New Orleans, LA (US)

(73) Assignee: Bausch & Lomb Incorporated, Rochester, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 07/844,879

(22) Filed: Mar. 3, 1992

Related U.S. Application Data

(63) Continuation of application No. 07/425,928, filed on Oct. 24, 1989, now abandoned, which is a continuation-in-part of application No. 07/370,095, filed on Jun. 22, 1989, now abandoned, which is a continuation of application No. 07/221,011, filed on Jul. 18, 1988, now abandoned, which is a continuation of application No. 06/866,302, filed on May 23, 1986, now abandoned, which is a division of application No. 06/760,080, filed on Jul. 29, 1985, now abandoned.

(51) Int. Cl.$^7$ .................................................. A61B 18/18
(52) U.S. Cl. .................................. 606/5; 606/3; 606/13; 606/15; 606/17
(58) Field of Search ...................... 128/395, 397, 128/398, 897–898; 602/2–19

(56) References Cited

U.S. PATENT DOCUMENTS

| | | | |
|---|---|---|---|
| 3,914,013 | 10/1975 | Rosenberg | 350/96 B |
| 3,982,541 | * 9/1976 | L'Esperance, Jr. | 606/4 |
| 4,383,843 | 5/1983 | Iyenger | 65/2 |
| 4,409,979 | 10/1983 | Roussel et al. | 128/303.1 |
| 4,445,892 | 5/1984 | Hussein et al. | 128/303.1 |
| 4,461,294 | 7/1984 | Baron | 128/303.1 |
| 4,469,098 | 9/1984 | Daui | 128/303.1 |
| 4,538,608 | * 9/1985 | L'Esperance, Jr. | 606/4 |
| 4,648,400 | 3/1987 | Schneider et al. | 128/303.1 |
| 4,665,913 | * 5/1987 | L'Esperance, Jr. | 606/11 |
| 4,669,466 | 6/1987 | L'Esperance | 128/303.1 |
| 4,676,790 | * 6/1987 | Kern | 606/166 |
| 4,718,418 | 1/1988 | L'Esperance, Jr. | 128/303.1 |
| 4,729,372 | 3/1988 | L'Esperance, Jr. | 128/303.1 |
| 4,732,148 | 3/1988 | L'Esperance, Jr. | 128/303.1 |
| 4,744,360 | * 5/1988 | Bath | 606/6 |
| 4,799,478 | * 1/1989 | Fedorow et al. | 606/28 |
| 4,903,695 | * 2/1990 | Warner et al. | 606/4 |
| 4,907,586 | * 3/1990 | Bille et al. | 606/5 |

FOREIGN PATENT DOCUMENTS

8707165 * 12/1987 (WO) ........................................ 606/5

OTHER PUBLICATIONS

"Excimer Laser RadialKeratotomy" by Cotliar et al, Opthalmology, 92: 206–208, Feb. 1985.

(List continued on next page.)

*Primary Examiner*—David M. Shay
(74) *Attorney, Agent, or Firm*—William Greener; Akin, Gump

(57) ABSTRACT

A method for modifying the curvature of a live cornea via use of a laser. The live cornea is first separated into first and and second opposed internal surfaces. Next, a laser beam is directed onto at least one of the first and second internal surfaces, or both. The laser beam is used to either ablate a three-dimensional portion of the cornea for making the cornea less curved, or coagulate a portion of the cornea for making the cornea more curved. In one embodiment, the central portion of the cornea is ablated to make the cornea less curved. In another embodiment, a plurality of internal tunnels are formed and ablated in the cornea to make the cornea less curved. In yet another embodiment, a plurality of internal points in the cornea forming the periphery of a circle are coagulated to make the cornea more curved. In place of the laser, a mechanical device can be used, such as a drill tip.

31 Claims, 7 Drawing Sheets

OTHER PUBLICATIONS

"Refractive Keratoplosty: Lathing and Cyropreservation", by Zavalo et al, CLAO Journal, 11:155 (Apr. 1985).

"Epikeratophakia : Techniques, Complications and Clinical Results", by Theodore P. Weblin, Ophthalmology pp45–58.

"Keratomileusis and Keratophakia in the Surgical Correction of Aphakia", by Barraquer, Cataract surgery and special techniques, pp 270–289.

Refractive Keratoplasty: Acute Morphologic Features; by Baumgartner et al, CLAO Journal, Apr. 1985 vol. 11 No. 2 pp 163–169.

"Adhesion of Regenerating Corneal Epithelium" by Khodadoust et al, Am. J. of Opthalmology, Mar. 1968 pp 339–348.

"Recurrent Corneal Erosion: Pathogenesis and Therapy", by Kenyon (1978) pp. 171–195.

"Prenatal Development of the Eye and its Adnexa" by Ozanics et al Biomedical Foundation of Opthalmology, vol. 1, Chap2, p7–15, (1985).

"Lamellan Corneal Stromectomy" by Krwawicz rec'd in PTO 9/86 pp 828–833.*

"Modification of Rabbit Corneal Curvature with use of Carbon Dioxide laser Burns" by Peyman et al; Ophth, Surg.;vol. 11,No. 5;5/80;pp325–329.*

"Excimer Laser Ablator of the Cornea & Lens" by C. Puliafito et al, Opthalmology 6/85 vol. 92 #6 pp.741–748.

"Excimer Laser Surgery of the Cornea" by S. Trokel et al, Am. J. Opthalmology, vol. 96, pp. 710–715, 1983.

"Corneal Surgery" by L. Girard, The C.V. Mosby Publishing Company, London, 1981, pp. 84,107–110, 114, 116, 123, 125–133, 143–171.

"Response of the Corneal Epithelium to K.F. Excimer Laser Pulses," by J. Taboda et al, Health Physics vol. 40, pp. 677–683, 1981.

"IBM's Heatless Laser Etching: A Hot IC & Medical Prospect", News Spectra, 6/83.

"Heatless Laser Etching" by J. Free, Popular Science 12/83, p. 114.

"A New Surgical Approach to Myopia" by Sato et al, American Journal of Opthlamology, 36:823 (1953).

"Keratomileusis for Myopia and Aphakia", by Barraquer Opthalmology, Aug. 1981, 88:701.

"UCLA Clinical Trial of Radial Keratotomy", by Hoffer et al, Opthalmology; Aug. 1981; 88:729.

* cited by examiner

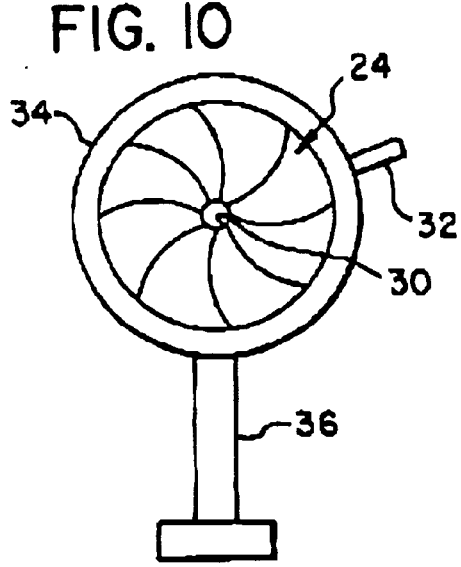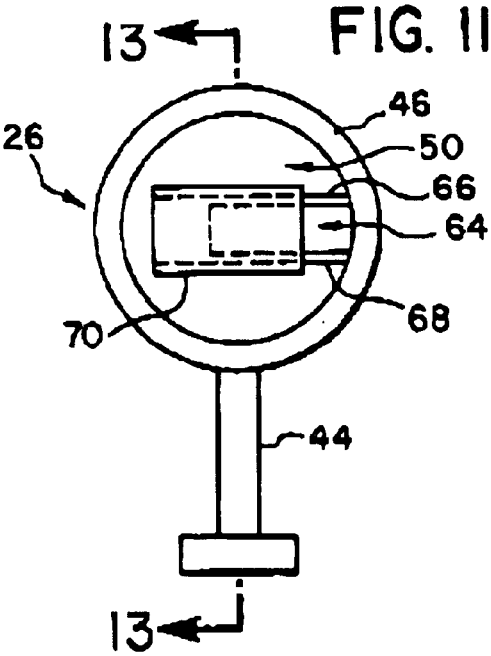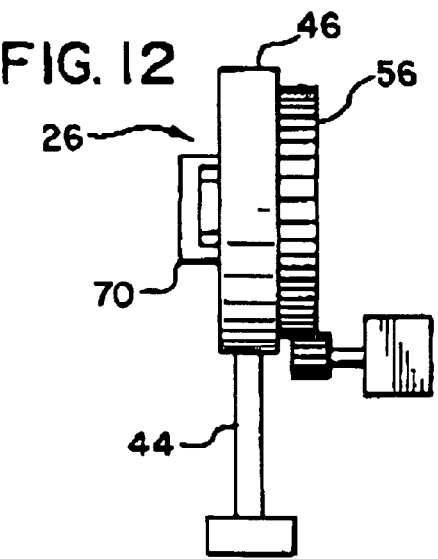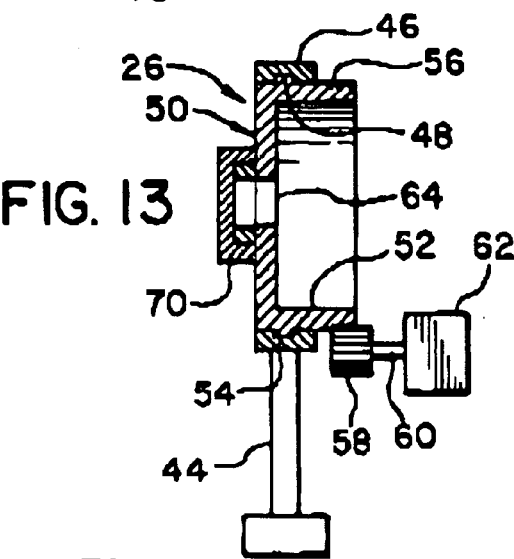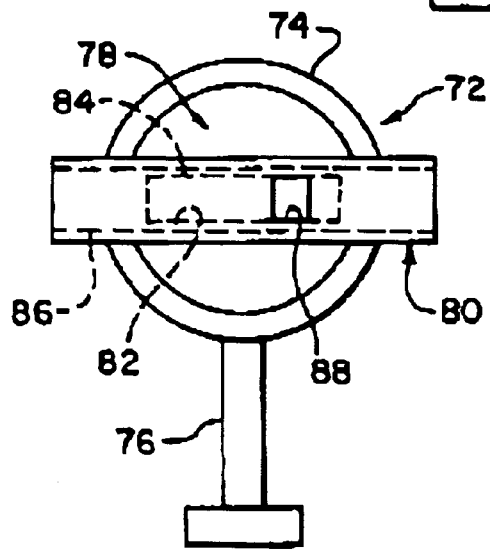

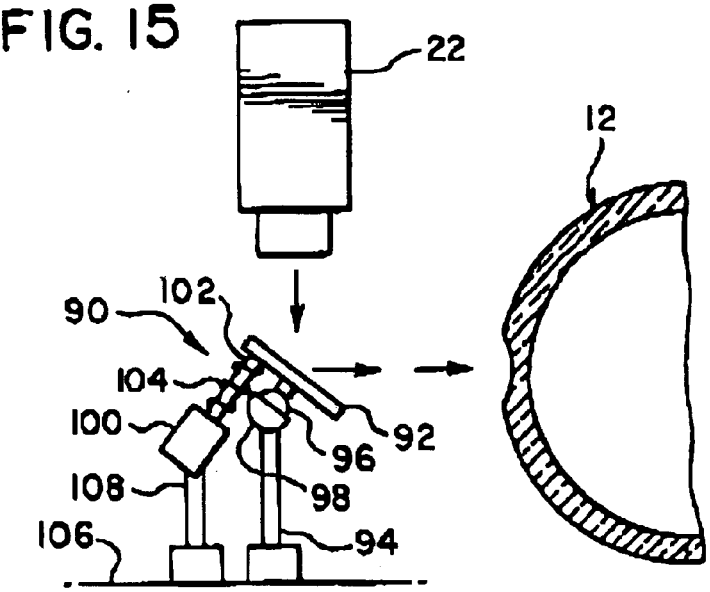
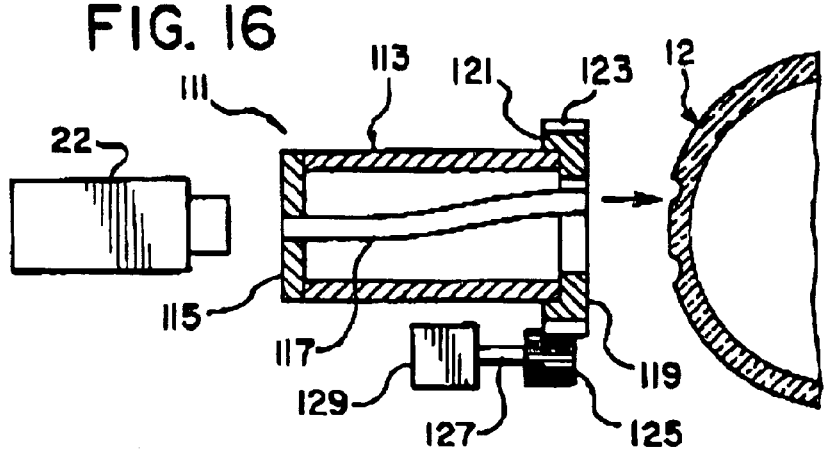
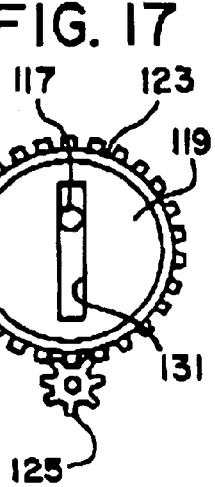
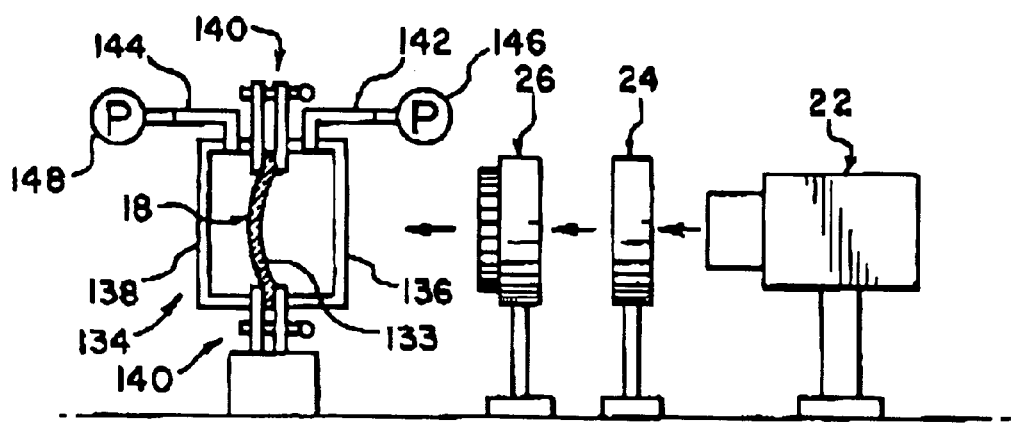

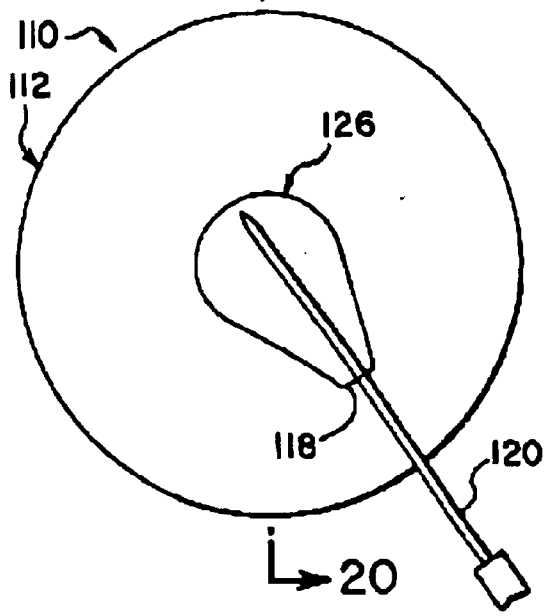
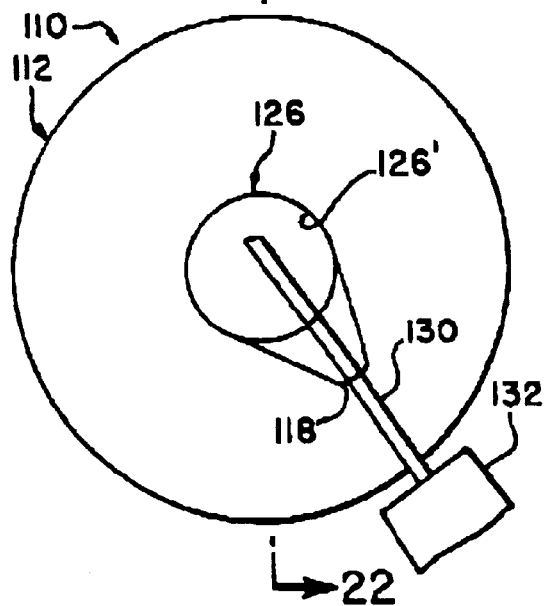
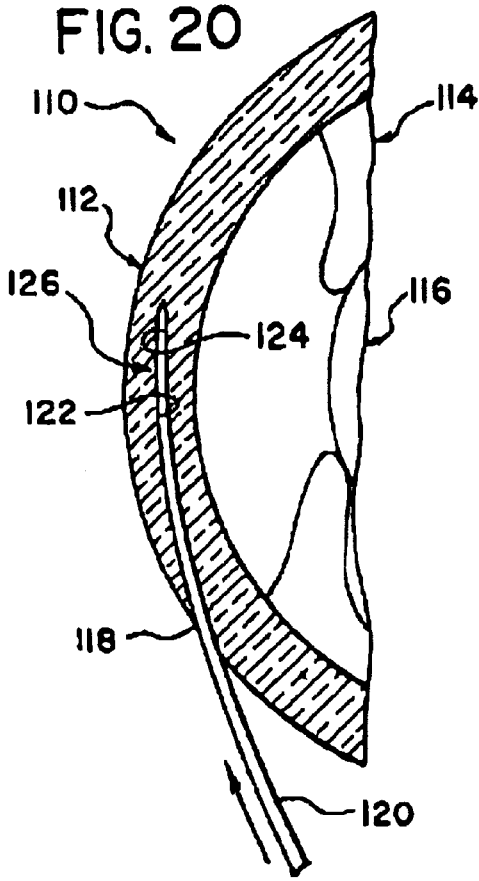
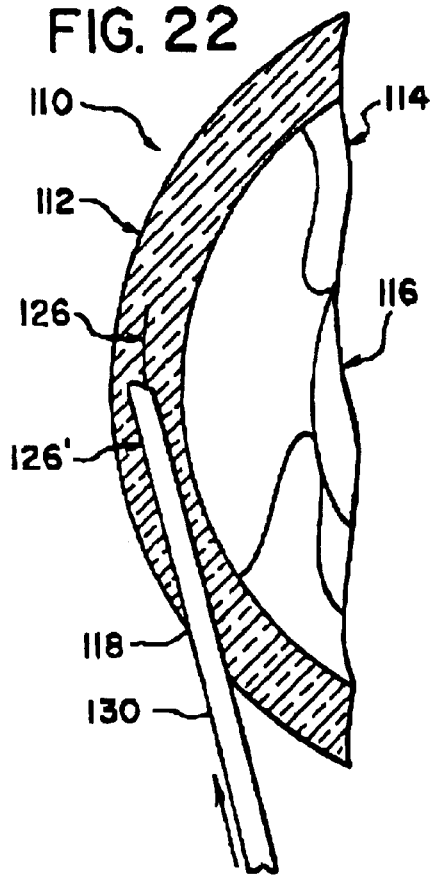

CORNEAL CURVATURE MODIFICATION VIA INTERNAL ABLATION

RELATED APPLICATIONS

This is a continuation of application Ser. No. 07/425,928 filed Oct. 24, 1989 now abandoned.

This is a continuation-in-part of application Ser. No. 07/370,095, filed Jun. 22, 1989, now abandoned which is a continuation of application Ser. No. 07/221,011, filed Jul. 18, 1988, now abandoned, which is a continuation of application Ser. No. 06/866,302, filed May 23, 1986, now abandoned, which is a division of application Ser. No. 06/760,080, filed Jul. 29, 1985, now abandoned.

FIELD OF THE INVENTION

The invention relates to a method and apparatus for modifying the curvature of a live cornea via a laser beam. In particular, the curvature of the live cornea is modified by the steps of separating an internal area of the live cornea into first and second opposed radially directed internal surfaces, then directing a laser beam onto at least one of the first and second internal surfaces to ablate or coagulate a portion of the cornea, and then recombining the first and second internal surfaces.

BACKGROUND OF THE INVENTION

In an emetropic human eye, the far point, i.e., infinity, is focused on the retina. Ametropia results when the far point is projected either in front of the retina, i.e., myopia, or in the back of this structure, i.e., hypermetropic or hyperopic state.

In a myopic eye, either the axial length of the eye is longer than in a normal eye, or the refractive power of the cornea and the lens is stronger than in emetropic eyes. In contrast, in hypermetropic eyes the axial length may be shorter than normal or the refractive power of the cornea and lens is less than in a normal eye. Myopia begins generally at the age of 5–10 and progresses up to the age of 20–25. High myopia greater than 6 diopter is seen in 1–2% of the general population. The incidence of low myopia of 1–3 diopter can be up to 10% of the population.

The incidence of hypermetropic eye is not known. Generally, all eyes are hypermetropic at birth and then gradually the refractive power of the eye increases to normal levels by the age of 15. However, a hypermetropic condition is produced when the crystalline natural lens is removed because of a cataract.

Correction of myopia is achieved by placing a minus or concave lens in front of the eye, in the form of glasses or contact lenses to decrease the refractive power of the eye. The hypermetropic eye can be corrected with a plus or convex set of glasses or contact lenses. When hypermetropia is produced because of cataract extraction, i.e., removal of the natural crystalline lens, one can place a plastic lens implant in the eye, known as an intraocular lens implantation, to replace the removed natural crystalline lens.

Surgical attempts to correct myopic ametropia dates back to 1953 when Sato tried to flatten the corneal curvature by performing radial cuts in the periphery of a corneal stroma (Sato, Am. J. Ophthalmol. 36:823, 1953). Later, Fyoderov (Ann. Ophthalmol. 11:1185, 1979) modified the procedure to prevent postoperative complications due to such radial keratotomy. This procedure is now accepted for correction of low myopia for up to 4 diopter (See Schachar [eds] Radial Keratotomy LAL, Pub. Denison, Tex., 1980 and Sanders D [ed] Radial Keratotomy, Thorofare, N.J., Slack publication, 1984).

Another method of correcting myopic ametropia is by lathe cutting of a frozen lamellar corneal graft, known as myopic keratomileusis. This technique may be employed when myopia is greater than 6 diopter and not greater than 18 diopter. The technique involves cutting a partial thickness of the cornea, about 0.26–0.32 mm, with a microkeratome (Barraquer, Ophthalmology Rochester 88:701, 1981). This cut portion of the cornea is then placed in a cryolathe and its surface modified. This is achieved by cutting into the corneal parenchyma using a computerized system. Prior to the cutting, the corneal specimen is frozen to −18° F. The difficulty in this procedure exists in regard to the exact centering of the head and tool bit to accomplish the lathing cut. It must be repeatedly checked and the temperature of the head and tool bit must be exactly the same during lathing. For this purpose, carbon dioxide gas plus fluid is used. However, the adiabatic release of gas over the carbon dioxide liquid may liberate solid carbon dioxide particles, causing blockage of the nozzle and inadequate cooling.

The curvature of the corneal lamella and its increment due to freezing must also be calculated using a computer and a calculator. If the corneal lamella is too thin, this results in a small optical zone and a subsequent dissatisfactory correction. If the tissue is thicker than the tool bit, it will not meet at the calculated surface resulting in an overcorrection.

In addition, a meticulous thawing technique has to be adhered to. The complications of thawing will influence postoperative corneal lenses. These include dense or opaque interfaces between the corneal lamella and the host. The stroma of the resected cornea may also become opaque (Binder Arch Ophthalmol 100:101, 1982 and Jacobiec, Ophthalmology [Rochester] 88:1251, 1981; and Krumeich JH, Arch, AOO, 1981). There are also wide variations in postoperative uncorrected visual acuity. Because of these difficulties, not many cases of myopic keratomileusis are performed in the United States.

Surgical correction of hypermetropic keratomyclosis involves the lamellar cornea as described for myopic keratomileusis. The surface of the cornea is lathe cut after freezing to achieve higher refractive power. This procedure is also infrequently performed in the United States because of the technical difficulties and has the greatest potential for lathing errors. Many ophthalmologists prefer instead an alternative technique to this procedure, that is keratophakia, i.e., implantation of a lens inside the cornea, if an intraocular lens cannot be implanted in these eyes.

Keratophakia requires implantation of an artificial lens, either organic or synthetic, inside the cornea. The synthetic lenses are not tolerated well in this position because they interfere with the nutrition of the overlying cornea. The organic lenticules, though better tolerated, require frozen lathe cutting of the corneal lenticule.

Problems with microkeratomies used for cutting lamellar cornea are irregular keritectomy or perforation of the eye. The recovery of vision is also rather prolonged. Thus, significant time is needed for the implanted corneal lenticule to clear up and the best corrective visions are thereby decreased because of the presence of two interfaces.

Application of ultraviolet and shorter wavelength lasers also have been used to modify the cornea. These lasers are commonly known as excimer lasers which are powerful sources of pulsed ultraviolet radiation. The active medium of these lasers are composed of the rare gases such as argon, krypton and xenon, as well as the halogen gases such as fluorine and chlorine. Under electrical discharge, these gases react to build excimer. The stimulated emission of the excimer produces photons in the ultraviolet region.

Previous work with this type of laser has demonstrated that far ultraviolet light of argon-fluoride laser light with the wavelength of 193 nm. can decompose organic molecules by breaking up their boundings. Because of this photoablative effect, the tissue and organic and plastic material can be cut without production of heat, which would coagulate the tissue. The early work in ophthalmology with the use of this type of laser is reported for performing radial cuts in the cornea in vitro (Trokel, Am. J. Ophthalmol 1983 and Cotliar, Ophthalmology 1985). Presently, all attempts to correct corneal curvature via lasers are being made to create radial cuts in the cornea for performance of radial keratotomy and correction of low myopia.

Because of the problems related to the prior art methods, there is a continuing need for improved methods to correct eyesight.

SUMMARY OF THE INVENTION

Accordingly, it is a primary object of the present invention to provide a method for modifying corneal curvature via removing a three-dimensional internal portion of the cornea.

Another object of the invention is to provide such a method that can modify the curvature of a live cornea, thereby eliminating the need and complications of working on a frozen cornea.

Another object of the invention is to provide a method for improving eyesight without the use of glasses or contact lenses, but rather by merely modifying the corneal curvature.

Another object of the invention is to provide a method for modifying corneal curvature by using a source of laser light in a precise manner.

Another object of the invention is to provide a method that can modify the curvature of a live cornea without the need of sutures.

Another object of the invention is to provide a method that can modify the curvature of a live cornea with minimal incisions into the epithelium of the cornea.

Another object of the invention is to provide a method for modifying the corneal curvature by ablating or coagulating the corneal stroma.

The foregoing objects are basically attained by a method of modifying the curvature of a patient's live cornea comprising the steps of separating an internal area of the live cornea into first and second opposed internal surfaces, the first internal surface facing in the posterior direction and the second internal surface facing in the anterior direction, directing a laser beam onto at least one of the first and second internal surfaces in a predetermined pattern to ablate, and therefore remove, a three-dimensional portion thereof, and recombining the first and second internal surfaces, the separating, directing and recombining steps taking place without freezing the cornea.

Other objects, advantages, and salient features of the present invention will become apparent from the following detailed description, which, taken in conjunction with the annexed drawings, discloses preferred embodiments of the invention.

BRIEF DESCRIPTION OF THE DRAWINGS

Referring now to the drawings which form a part of this original disclosure:

FIG. 10 is a front elevational view of the adjustable diaphragm shown in FIG. 3 used for directing the laser beam towards the eye;

FIG. 11 is a front elevational view of the guiding mechanism shown in FIG. 3 having a rotatable orifice of variable size formed therein, for directing the laser beam towards the eye in a predetermined pattern;

FIG. 12 is a right side elevational view of the guiding mechanism shown in FIG. 11;

FIG. 13 is a right side elevational view in section taken along line 13—13 in FIG. 11 showing the internal parts of the guiding mechanism;

FIG. 14 is a front elevational view of a modified guiding mechanism including a movable orifice;

FIG. 15 is a diagrammatic side elevational view of a second modified guiding mechanism for a laser beam including a universally supported mirror and actuating motors used for moving the mirror and thereby guiding the laser beam in the predetermined pattern;

FIG. 16 is a diagrammatic side elevational view of a third modified guiding mechanism comprising a housing and a rotatable fiber optic cable;

FIG. 17 is an end elevational view of the housing and fiber optic cable shown in FIG. 16;

FIG. 18 is a diagrammatic side elevational view of a laser source, diaphragm and guiding mechanism for use in ablating the thin layer removed from the cornea, which is shown supported by a pair of cups;

FIG. 19 is a front elevational view of a live cornea which has been cut with a spatula to separate the central portion of the cornea into first and second opposed internal surfaces in accordance with the present invention;

FIG. 20 is a side elevational view in section taken along line 20—20 of the cornea shown in FIG. 19;

FIG. 21 is a front elevational view of a cornea that has been cut as shown in FIG. 19 with ablation conducted in the central portion of the cornea by a laser;

FIG. 22 is a side elevational view in section taken along line 22—22 of the cornea shown in FIG. 21;

DETAILED DESCRIPTION OF THE INVENTION

Figure 1:
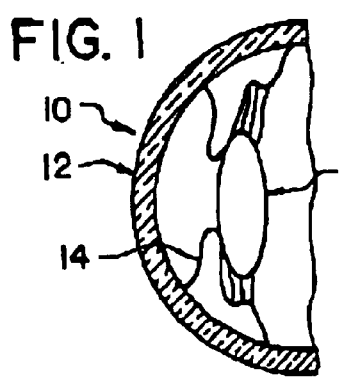
FIG. 1 is a side elevational view in section taken through the center of an eye showing the cornea, pupil and lens.
Figure 2:
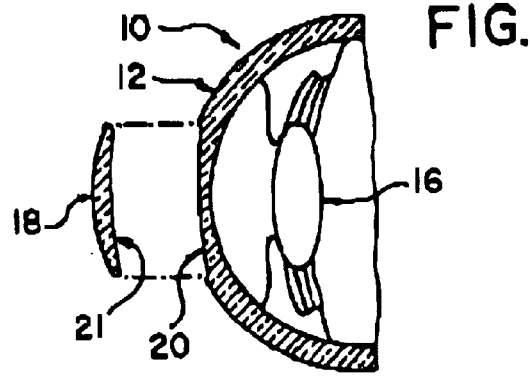
FIG. 2 is a side elevational view in section similar to that shown in FIG. 1 except that a thin layer has been removed from the front of the cornea, thereby separating the cornea into first and second opposed internal surfaces.

As seen in FIG. 1, an eye 10 is shown comprising a cornea 12, a pupil 14, and a lens 16. If the combination of the cornea and lens does not provide adequate vision, the cornea can be modified in accordance with the invention to modify the refractive power of the combined corneal and lens system, to thereby correct vision. This is accomplished first by removing a thin layer 18 from the center part of a patient's live cornea 12 by cutting via a means for removing 19, such as a scalpel, via cutting, this thin layer being on the order of about 0.2 mm in thickness with the overall cornea being about 0.5 mm in thickness. Once the thin layer 18 is cut and removed from the cornea, it exposes first and second opposed internal surfaces 20 and 21 resulting from the surgical procedure. Advantageously, it is the exposed internal surface 20 on the remaining part of the cornea that is the target of the ablation via the excimer laser. On the other hand, the cut internal surface 21 on the removed thin layer of the cornea can also be the target of the laser, as illustrated in FIG. 18 and discussed in further detail hereinafter.

Figure 3:
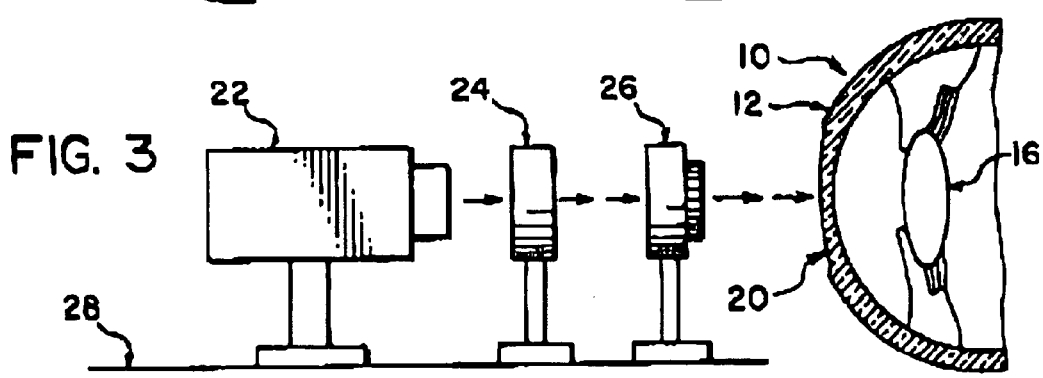
FIG. 3 is a diagrammatic side elevational view of the eye shown in FIG. 2 with a laser beam source, diaphragm and guiding mechanism being located adjacent thereto.

As seen in FIG. 3, the apparatus used in accordance with the invention comprises a source of a laser beam 22, an adjustable diaphragm 24, and a guiding mechanism 26, all aligned adjacent the eye 10 and supported on a suitable base 28.

The laser beam source 22 is advantageously an excimer laser of the argon-fluoride or krypton-fluoride type. This type of laser will photoablate the tissue of the cornea, i.e., decompose it without burning or coagulating which would unduly damage the live tissue. This ablation removes desired portions of the cornea and thereby allows for modification of the curvature thereof.

The adjustable diaphragm 24 seen in FIGS. 3 and 10 is essentially a conventional optical diaphragm with an adjustable central orifice 30 that can be increased or decreased in radial size by a manipulation of a lever 32 coupled to the diaphragm. The diaphragm is advantageously supported in a ring 34 that is in turn supported on a stand 36 on base 28. The material forming the diaphragm is opaque to laser light and thus when the laser is directed towards the diaphragm, it will pass therethrough only via the orifice 30. The diaphragm 24 can be used in conjunction with the guiding mechanism 26, to be described in more detail hereinafter, to restrict the size of the laser beam passing to the guiding mechanism 26, or it can be used by itself to provide ablation of the exposed internal surface 20 of a cornea at its center.

Figure 7:
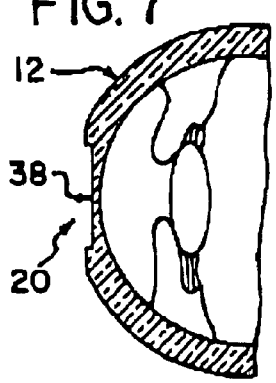
FIG. 7 is a side elevational view in section of an eye which has been ablated in the central area of the internal surface on the cornea.
Figure 8:
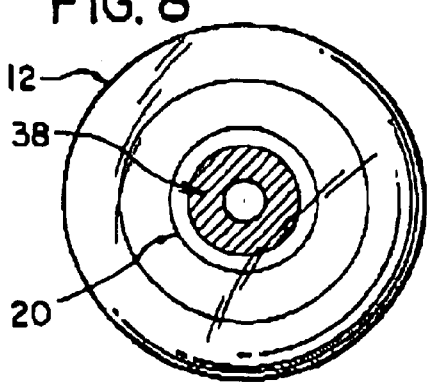
FIG. 8 is a front elevational view of the cornea having the central ablated portion shown in FIG. 7.
Figure 9:
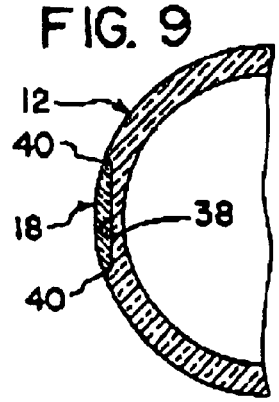
FIG. 9 is a side elevational view in section of the ablated cornea of FIGS. 7 and 8 in which the thin layer previously removed from the cornea is replaced over the ablated area, thereby reducing the curvature of the overall cornea.

This is illustrated in FIGS. 7–9 where a substantially disc-shaped ablated portion 38 is formed in the central exposed internal surface 20 by directing the laser beam 22 through orifice 30 of the diaphragm 24. By modifying the size of the orifice, the disc-shaped ablated portion 38 can be varied in size. Also, by varying the size of the orifice over time, either a concave or convex ablated portion can be formed, as desired. As shown in FIG. 9, once the ablated portion 38 is as desired, the previously removed thin layer 18 is replaced onto the cornea in the ablated portion 38 and can be connected thereto via sutures 40.

Because the ablated portion 38 as seen in FIG. 7 is essentially a uniform cylindrical depression in the exposed internal surface 20, when the thin corneal layer 18 is replaced, the curvature of the cornea is decreased, thereby modifying the refractive power of the cornea and lens system.

As seen in FIG. 10, lever 32 is used to vary the size of orifice 30, and is capable of being manipulated by hand or by a suitable conventional motor, which can be coordinated to provide an expansion or contraction of the orifice as necessary over time.

As seen in FIGS. 3, 11, 12 and 13, the guiding mechanism 26 can be utilized in addition to or in place of the diaphragm 24 to guide the laser light onto the cornea. This guiding mechanism 26 is especially advantageous for forming an annular ablated portion 42 in surface 20 as seen in FIGS. 4–6 for increasing the overall curvature of the cornea.

Figure 4:
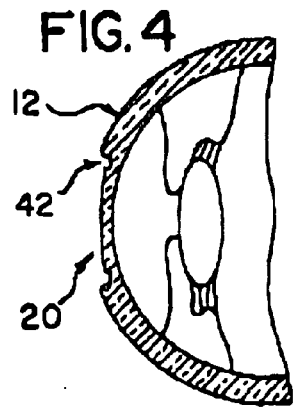
FIG. 4 is a side elevational view in section of an eye that has been treated by the apparatus shown in FIG. 3 with ablation conducted in an annular area spaced from the center of the internal surface on the cornea.
Figure 5:
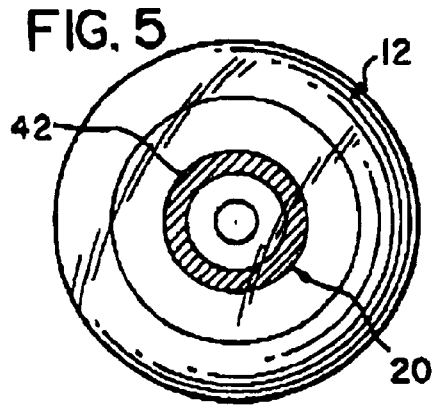
FIG. 5 is a front elevational view of the ablated cornea shown in FIG. 4.
Figure 6:
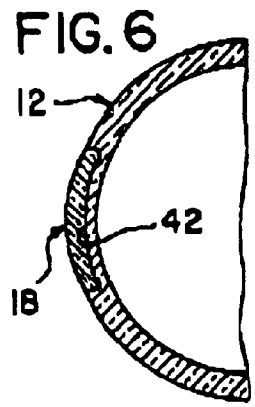
FIG. 6 is a side elevational view in section showing the ablated cornea of FIGS. 4 and 5 with the thin layer previously removed from the cornea replaced onto the ablated area in the cornea, thereby increasing the curvature of the overall cornea.

As seen in FIGS. 4 and 5, this annular ablated portion 42 is spaced from the center of the exposed internal surface 20 and when the previously removed thin corneal layer 18 is replaced and sutured, the thin layer tends to be more convex, thereby modifying the overall curvature of the cornea.

As seen in FIGS. 11–13, the guiding mechanism 26 comprises a stand 44 supporting a ring 46, this ring having a radially inwardly facing recess 48 therein. A disc 50, which is opaque to laser light, is located inside the ring and has a cylindrical extension 52 with an outwardly facing flange 54 rotatably and slidably received in the recess. On the cylindrical extension 52 which extends past ring 46 is an exterior toothed gear 56 that is in engagement with a pinion 58 supported on a shaft 60 of a motor 62. Rotation of pinion 58 in turn rotates gear 56 and disc 50.

The disc 50 itself has an elongated rectangular orifice 64 formed therein essentially from one radial edge and extending radially inwardly past the center point of the disc. Adjacent the top and bottom of the orifice 64 are a pair of parallel rails 66 and 68 on which a masking cover 70, which is U-shaped in cross section, is slidably positioned. Thus, by moving the masking cover 70 along the rails, more or less of the orifice 64 is exposed to thereby allow more or less laser light to pass therethrough and onto the cornea. Clearly, the larger the orifice, the larger the width of the annular ablated portion 42 will be. By rotating the disc, the orifice 64 also rotates and thus the annular ablated portion 42 is formed.

Embodiment of FIG. 14

Referring now to FIG. 14, a modified guiding mechanism 72 is shown which is similar to guiding mechanism 26 shown in FIGS. 11–13 except that the size of the orifice is not variable. Thus, the modified guiding mechanism 72 is comprised of a ring 74 on a stand 76, an opaque disc 78 which is rotatable in the ring via a suitable motor, not shown, and a slidable masking cover 80. Disc 78 has a rectangular orifice 82 extending diametrically thereacross with parallel rails 84 and 86 on top and bottom for slidably receiving the masking cover 80 thereon, this cover being U-shaped for engagement with the rails. The masking cover 80 has its own orifice 88 therein which aligns with orifice 82 on the disc. Thus, by sliding the masking cover 80 along the rails of the disc, the location of the intersection of orifice 88 and orifice 82 can be varied to vary the radial position of the overall through orifice formed by the combination of these two orifices. As in guiding mechanism 26, the masking cover 80 and disc 78 are otherwise opaque to laser light except for the orifices.

Embodiment of FIG. 15

Referring now to FIG. 15, a second modified guiding mechanism 90 is shown for directing laser light from laser beam source 22 to the cornea 12 along the desired predetermined pattern. This guiding mechanism 90 comprises a mirror 92 universally supported on a stand 94 via, for example, a ball 96 and socket 98 joint. This mirror 92 can be pivoted relative to the stand through the universal joint by means of any suitable devices, such as two small piezoelectric motors which engage the mirror at 90° intervals. For example, such a piezoelectric motor 100 having a plunger 102 coupled thereto and engaging the rear of the mirror can be utilized with a spring 104 surrounding the plunger and maintaining the mirror in a null position. The motor 100 is rigidly coupled to a base 106 via a stand 108. The second piezoelectric motor, not shown, can be located so that its plunger engages the rear of the mirror 90° from the location of motor 100. By using these two motors, springs and plungers, the mirror 92 can be fully rotated in its universal joint to direct the laser beam from source 22 onto the cornea 12 to ablate the cornea in a predetermined pattern.

Embodiment of FIGS. 16–17

Referring now to FIGS. 16 and 17, a third modified guiding mechanism 111 is shown for ablating a cornea 12 via directing laser light from laser source 22. This modified guiding mechanism 111 basically comprises a cylindrical housing 113 having an opaque first end 115 rotatably receiving the end of a fiber optic cable 117 therein. The second end 119 of the housing comprises a rotatable opaque disc having a flange 121 engaging the housing and an external gear 123 which in turn engages pinion 125, which is driven via shaft 127 and motor 129. Thus, rotation of the pinion results in rotation of gear 123 and thus the opaque second end 119 of the housing. This second end 119 has a diametrically oriented rectangular orifice 131 therein which receives the other end of the fiber optic cable 117 therein. That end of the fiber optic cable is either dimensioned so that it fits fairly tightly into the orifice or there is an additional suitable assembly utilized for maintaining the fiber optic cable end in a predetermined position in the orifice during rotation of the second end. However, this end would be movable radially of the orifice to change the position of the annular ablated portion formed by utilizing this guiding mechanism.

Referring now to FIG. 18, rather than ablating the exposed internal surface 20 on the cornea 12, the inner surface 133 of the removed thin corneal layer 18 can be ablated utilizing the apparatus shown in FIG. 18. Likewise, the apparatus of FIG. 18 can be used on an eye bank cornea removed from the eye and then positioned in the patient's eye to modify the curvature of the patient's combined corneal structure. This apparatus as before includes the source of the laser light 22, an adjustable diaphragm 24, and a guiding mechanism 26. In addition, an assembly 134 is utilized to support the rather flimsy removed thin corneal layer. This assembly 134 comprises a pair of laser light transparent cups 136 and 138 that are joined together in a sealing relationship via clamps 140 and engage therebetween the outer periphery of the thin corneal layer 18. Each of the cups has an inlet pipe 142, 144 for injecting pressurized air or suitable fluid into each via pumps 146 and 148. By using this pressurized container, the thin corneal layer 18 is maintained in the desired curvature so that the laser beam can provide a precise ablated predetermined pattern therein. In order to maintain the curvature shown in FIG. 8, the pressure on the right hand side of the thin layer is slightly greater than that on the left hand side.

Once the thin corneal layer 18 is suitably ablated as desired, it is replaced on the exposed internal surface 20 of the cornea and varies the curvature of the overall cornea as described above and illustrated in FIGS. 4–9.

Embodiment of FIGS. 19–27

Referring now to FIGS. 19–27, a patient's live in situ eye 110 is shown for the treatment of myopia in accordance with the present invention. Eye 110 includes a cornea 112, a pupil 114, and a lens 116, and is treated in accordance with the present invention without freezing the cornea.

Correction of myopia can be achieved by decreasing the curvature of the outer surface of cornea 112 (i.e., flattening the central portion of the cornea). This is accomplished by first cutting an incision 118 into the epithelium of cornea 112. Incision 118 may be curved or straight, and is preferably about 2.0–3.0 mm long and about 3.0–6.0 mm away from the center of cornea 112. A laser or spatula (i.e., a double-edge knife) may be used to make incision 118 in cornea 112.

As seen in FIGS. 19 and 20, once incision 118 is made, a spatula 120 is inserted into incision 118 to separate an internal area of live cornea 112 into first and second opposed internal surfaces 122 and 124, thereby creating an intrastromal or internal pocket 126. First internal surface 122 faces in the posterior direction of eye 110, while second internal surface 124 faces in the anterior direction of eye 110, and both of these surfaces extend radially relative to the center of the cornea.

As seen in FIGS. 19 and 20, pocket 126 is created by moving spatula 120 back and forth within an intrastromal area of cornea 112. It is important when creating pocket 126 to keep spatula 120 in substantially a single plane and substantially tangential to the cornea's internal surfaces to prevent intersecting and rupturing the Bowman's membrane.

Preferably, spatula 120 is about 3.0–12.0 mm long with a thickness of about 0.1–1.0 mm, and a width of about 0.1–1.2 mm. Spatula 120 may be slightly curved, as seen in FIG. 20, or may be straight.

While a spatula 120 is shown in FIGS. 19 and 20 for separating the internal surfaces of cornea 112, a fiber optic cable coupled to a laser beam source may be used instead of spatula 120 to separate cornea 112 into first and second opposed internal surfaces 122 and 124.

As seen in FIGS. 21 and 22, after pocket 126 is formed, a fiber optic cable tip 130 coupled to a fiber optic cable 132, which is in turn coupled to a laser, is then inserted through incision 118 and into pocket 126 for ablating a substantially circular area of cornea 112, thereby removing a substantially disc-shaped portion of cornea 112 to form a disc-shaped cavity 126'. The laser beam emitted from tip 130 may be directed upon either first internal surface 122, second internal surface 124, or both, and removes three-dimensional portions therefrom via ablation. The fiber optic cable can be solid or hollow as desired.

The laser source for fiber optic cable 132 is advantageously a long wavelength, infrared laser, such as a $CO_2$ or an erbium laser, or a short wavelength, UV-excimer laser of the argon-fluoride or krypton-fluoride type. This type of laser will photoablate the intrastromal tissue of the cornea, i.e., decompose it without burning or coagulating.

Figure 25:
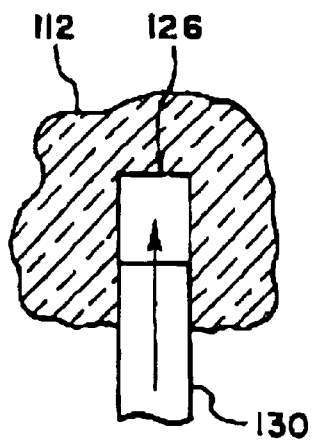
FIG. 25 is an enlarged, partial cross-sectional view of a cornea with a fiber optic tip cutting, separating and ablating the cornea into first and second opposed internal surfaces.
Figure 26:
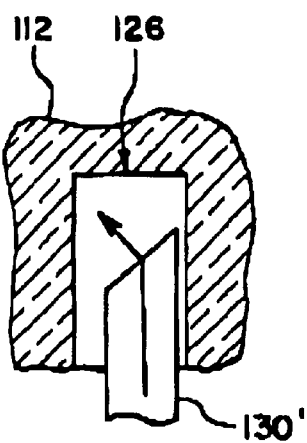
FIG. 26 is an enlarged, partial cross-sectional view of a cornea with a fiber optic tip having an angled end for ablating the cornea.
Figure 27:
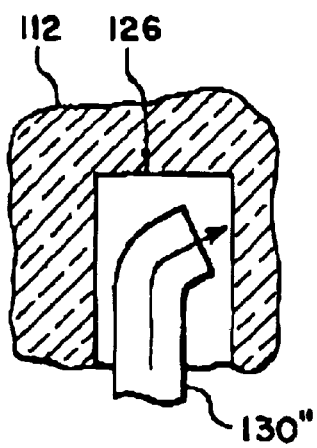
FIG. 27 is an enlarged, partial cross-sectional view of a cornea with a fiber optic tip having a bent end for ablating the cornea.
Figure 28:
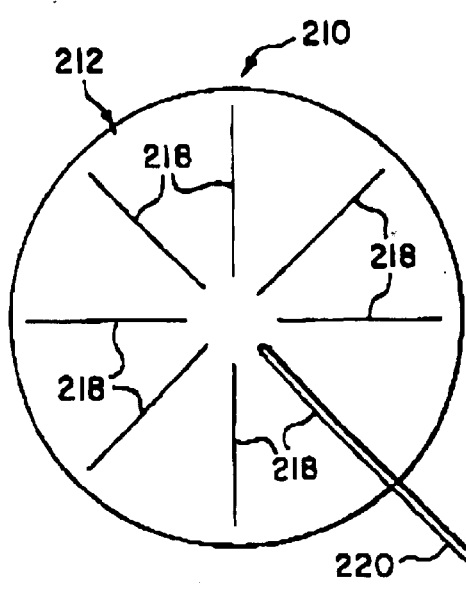
FIG. 28 is a front elevational view of a live cornea in which a plurality of radially extending cuts have been made with a spatula to separate the cornea at each of the radially extending cuts into first and second opposed internal surfaces in accordance with the present invention.
Figure 29:
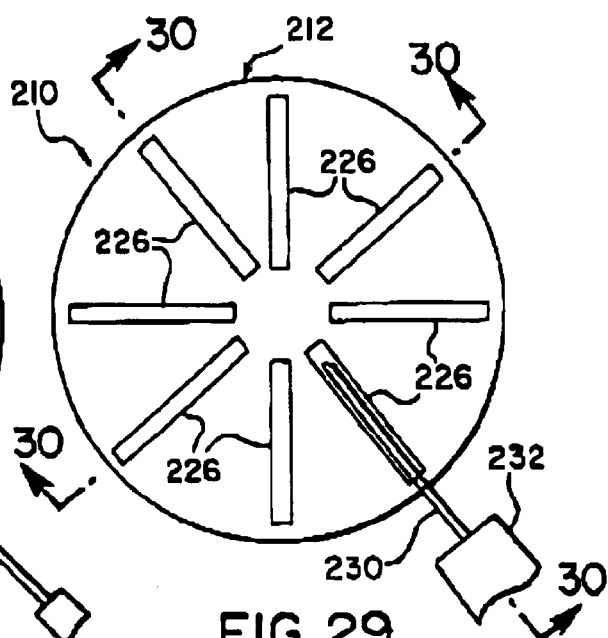
FIG. 29 is a front elevational view of a cornea in which the radially extending cuts shown in FIG. 28 have been ablated to create a plurality of radially extending tunnels.

FIGS. 25–27 illustrate three different configurations of the tip of a fiber optic cable for ablating the cornea. In FIG. 25, tip 130 has a substantially straight end for directing the laser beam parallel to the tip. As seen in FIG. 26, tip 130' has an end with an angled surface for directing the laser beam at an acute angle of preferably 45° relative to the tip to aid in ablating the cornea as desired. In FIG. 27, tip 130" has a curved end for bending the laser beam to aid ablating the cornea as desired.

Figure 23:
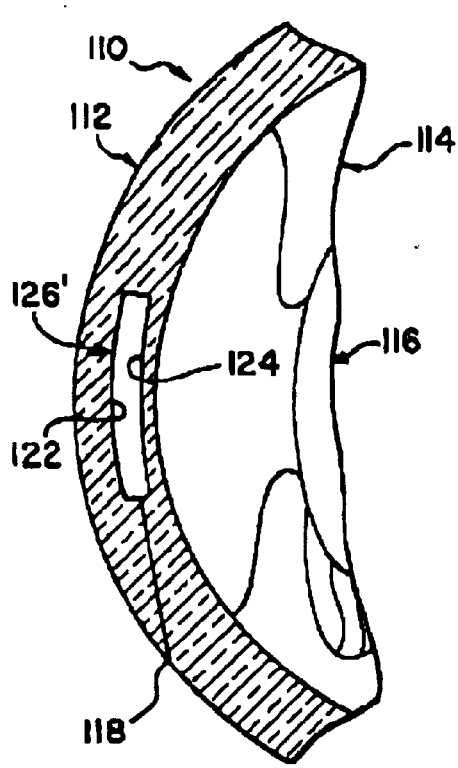
FIG. 23 is a side elevational view in section taken through the center of an eye showing the ablated cornea of FIGS. 19–22 with the fiber optic tip removed.

As seen in FIG. 23, cornea 112 is shown with the substantially disc-shaped cavity 126' formed at the center of cornea 112 just after tip 130 has been removed and prior to cornea 112 collapsing or flattening. The disc-shaped cavity 126' can be varied in size and shape, depending upon the amount of curvature modification needed to correct the patient's eyesight. Accordingly, any three-dimensional intrastromal area of the cornea may be removed to modify the cornea as desired.

Figure 24:
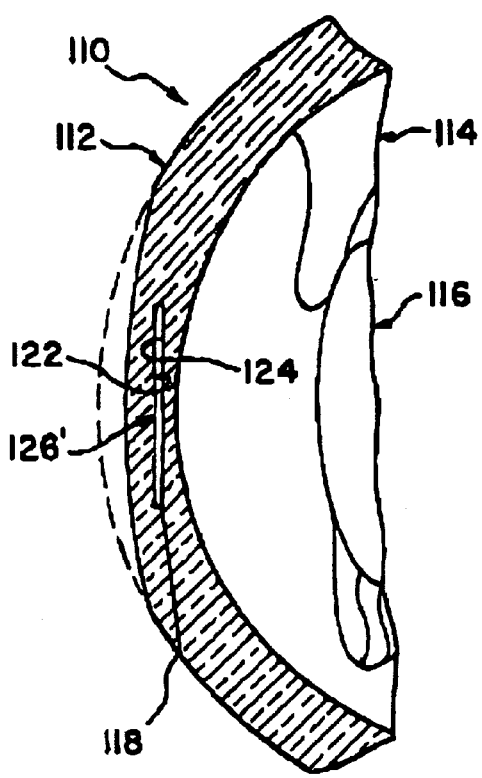
FIG. 24 is a side elevational view in section taken through the center of an eye showing the ablated cornea of FIGS. 19–23 in its collapsed position, thereby decreasing the curvature of the central portion of the cornea.

As seen in FIG. 24, after pocket 126 is ablated and tip 130 removed, the ablated cavity 126' then collapses under normal eye pressure to recombine ablated first and second internal surfaces 122 and 124 together. This collapsing and recombining of the intrastromal area of the cornea decreases the curvature of the central portion of cornea 112 from its original shape shown in broken lines to its new shape as seen in FIG. 24. After a period of time, depending on the patient's healing abilities, the ablated surfaces heal and grow back together, resulting in a permanent modification of the cornea's curvature.

Embodiment of FIGS. 28–31

Referring now to FIGS. 28–31, an eye 210 is shown for the treatment of myopia in accordance with another embodiment of the present invention, and includes a cornea 212, a pupil 214, and a lens 216, the cornea being treated without freezing it. In this embodiment, correction of myopia is accomplished by first making a plurality of radially directed intrastromal incisions 218 with a flat pin or blade spatula 220. These incisions 218 separate the cornea 218 into first and second opposed internal surfaces 222 and 224 at each of the incisions 218. First internal surfaces 222 face in the posterior direction of eye 210, while second internal surfaces 224 face in the anterior direction of eye 210, and both extend radially relative to the center of the cornea. Spatula 220 may have a straight or curved blade with a maximum diameter of about 0.1–0.2 mm. A laser may be used instead of spatula 220 to make incisions 218, if desired.

Incisions or unablated tunnels 218 extend generally radially towards the center of cornea 212 from its periphery. Preferably, incisions 218 stop about 3.0 mm from the center of cornea 212, although incisions 218 may extend to the center of cornea 212, depending upon the degree of myopia. Incisions 218 will normally extend about 3.0–10.0 mm in length, again depending on the amount of change desired in curvature of cornea 112. While only radial incisions have been shown, it will be apparent to those skilled in the art that the incisions may be non-radial, curved, or other shapes. When creating incisions 218, it is important to keep the spatula 220 in substantially a single plane so as not to intersect and puncture the Bowman's membrane.

Once intrastromal incisions 218 have been created with spatula 220, a fiber optic cable tip 230 coupled to a fiber optic cable 232 and a laser is then inserted into each of the incisions 218 for ablating tunnels 226 to the desired size. The laser beam emitted from tip 230 may be directed upon either first internal surface 222, second internal surface 224, or both for ablating tunnels 226 and removing three-dimensional portions from these surfaces.

The laser source for cable 232 is advantageously similar to the laser source for cable 132 discussed above.

Figure 30:
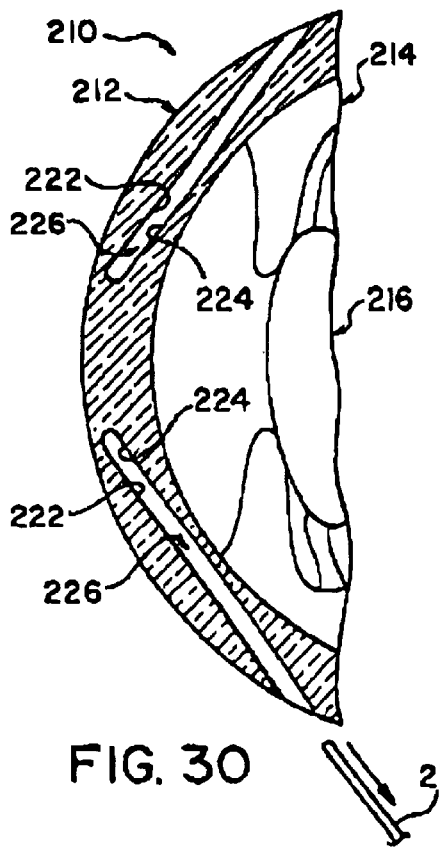
FIG. 30 is a side elevational view in section taken along line 30—30 of the cornea of FIG. 29 with the fiber optic tip removed.
Figure 31:
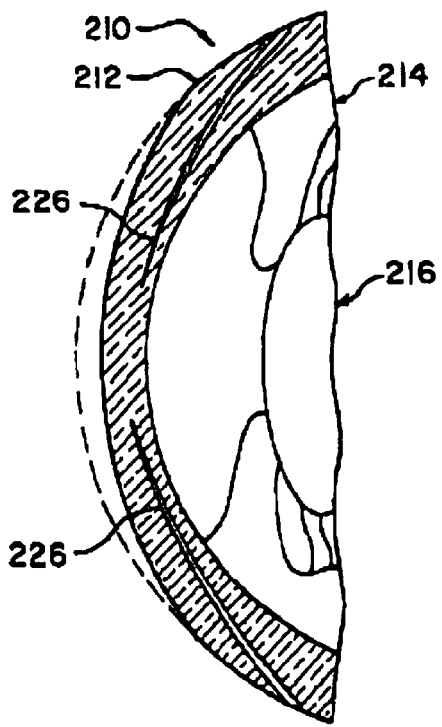
FIG. 31 is a side elevational view in section taken along the center of an eye showing the ablated cornea of FIGS. 28–30 in its collapsed position, thereby decreasing the curvature of the central portion of the cornea.

Referring now to FIGS. 30 and 31, a pair of ablated tunnels 226 are shown. In FIG. 30, cornea 212 is shown with ablated tunnels 226 just after tip 230 has been removed and prior to tunnels 226 collapsing or flattening. In FIG. 31, cornea 212 is shown after ablated tunnels 226 have collapsed to recombine first and second internal surfaces 222 and 224, thereby flattening cornea 212. In other words, this collapsing and recombining of the intrastromal area of the cornea decreases the curvature of the central portion of cornea 212 from its original shape shown in broken lines to its new shape as seen in FIG. 31.

By collapsing intrastromal tunnels, this allows the outer surface of the cornea to relax, i.e., decrease surface tension, thereby permitting flattening of the cornea.

Embodiment of FIGS. 32–35

Referring now to FIGS. 32–35, an eye 310 is shown for the treatment of hyperopia in accordance with another embodiment of the present invention. Eye 310 includes a cornea 312, a pupil 314, and a lens 316. Correction of hyperopia can be achieved by increasing the curvature of the outer surface of cornea 312 (i.e., making the central portion of the cornea more curved), without freezing the cornea.

This is accomplished by making a plurality of intrastromal incisions or tunnels 318 with a spatula 320 to form first and second opposed internal surfaces 322 and 324. Tunnels 318 extend substantially radially towards the center of cornea 312. While eight equally spaced, radial tunnels 318 are shown, it will be apparent to those skilled in the art that more or fewer tunnels with varying distances apart may be made, depending upon the amount of curvature modification needed.

The initial step of making incisions or tunnels 318 of FIGS. 32–35 is similar to the initial step of making incisions 218 of FIGS. 28–31. Accordingly, spatula 320 is similar to spatula 220 discussed above. Likewise, a laser may be used to make incisions or tunnels 318 instead of spatula 320.

Figures 32, 34:
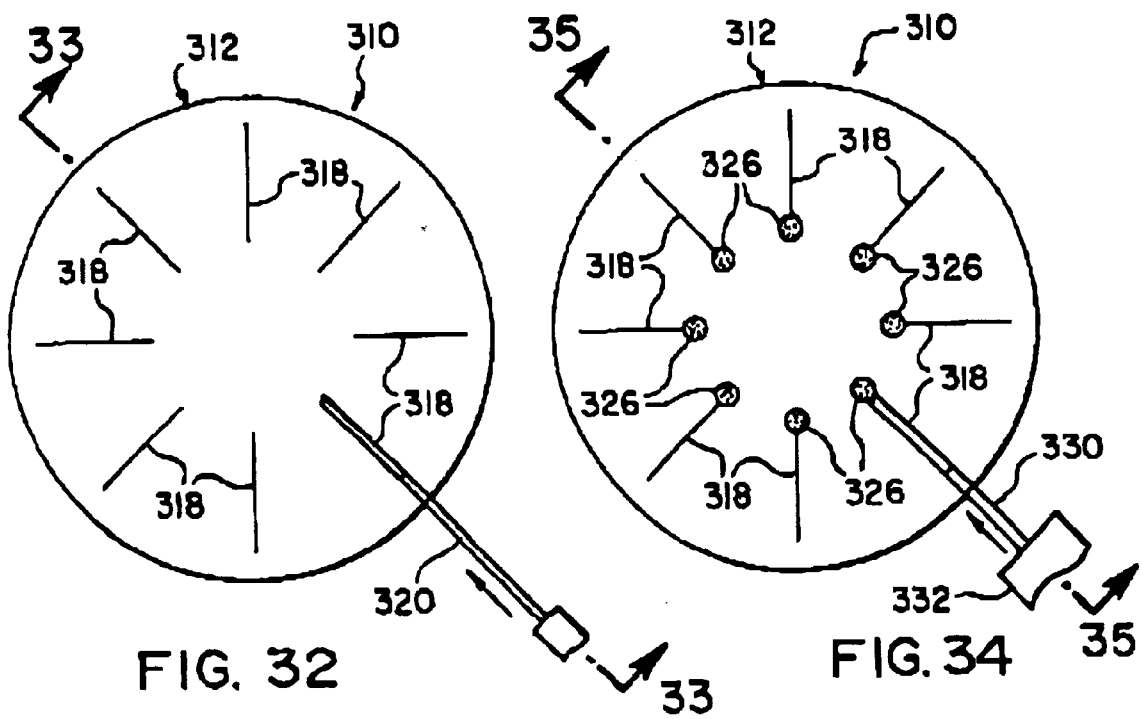
FIG. 32 is a front elevational view of a live cornea in which a plurality of radially extending cuts have been made with a spatula to separate the cornea at each of the radially extending cuts into first and second opposed internal surfaces in accordance with the present invention.
FIG. 34 is a front elevational view of a cornea that has been radially cut as shown in FIGS. 32 and 33 with coagulation conducted at the ends of the radial cuts by a laser, thereby increasing the curvature of the central portion of the cornea.

Once tunnels 318 are created, a fiber optic cable tip 330 extending from fiber optic cable 332 is inserted into each tunnel 318 to direct a laser beam on either first internal surface 322, second internal surface 324, or both internal surfaces to coagulate an intrastromal portion of cornea 312. As seen in FIG. 34, a point 326 at the end of each of the tunnels 318 is coagulated. Preferably, coagulation points 326 lie substantially on the circumference of a circle concentric with the center of cornea 312. The size of the circle forming coagulation points 326 depends upon the amount of curvature modification needed. Likewise, the number of coagulation points and their positions in the cornea depend upon the desired curvature modification needed.

Figures 33, 35, 36:
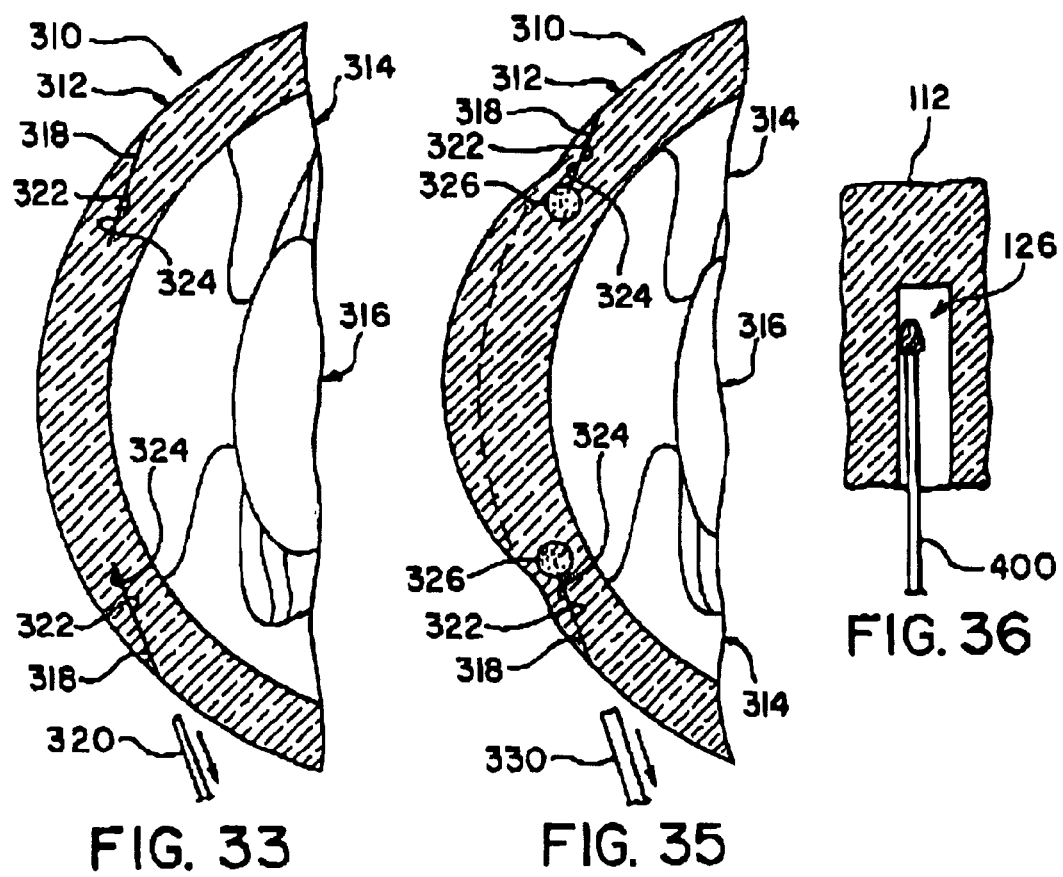
FIG. 33 is a side elevational view in section taken along line 33—33 of the cornea of FIG. 32 with the spatula removed.
FIG. 35 is a side elevational view in section taken along line 35—35 of the cornea of FIG. 34 with the laser removed and coagulation conducted at the ends of the radial cuts to increase the curvature of the central portion of the cornea.
FIG. 36 is an enlarged, partial cross-sectional view of a cornea with a drill tip removing tissue therefrom.

Coagulating intrastromal points of the cornea 312, such as coagulation points 326, with a laser causes those points of the cornea, and especially the collagen therein, to heat up and shrink. This localized shrinkage of the intrastromal portion of the cornea causes the outer surface of the cornea to be tightened or pulled in a posterior direction at each of the coagulation points, and thereby causes an increase in the overall curvature of the cornea as seen in FIG. 35. Coagulation, rather than ablation, is accomplished by using a laser having a wavelength which essentially cooks the corneal tissue and which is between the wavelengths associated with long infrared light and short ultraviolet light.

Embodiment of FIG. 36

As seen in FIG. 36, rather than using a laser to remove corneal tissue in the cavities 126 formed in the cornea 112 or to form those cavities, a rotating drill tip 400 suitably coupled to a rotary power source can be used to ablate the tissue by cutting. Likewise, any other suitable mechanical device can be used to remove the corneal tissue or form the cavities. A suitable evacuation device, such as a vacuum tube, can also be used to aid in evacuating from the cavity the tissue removed from the cornea.

While various advantageous embodiments have been chosen to illustrate the invention, it will be understood by those skilled in the art that various changes and modifications can be made therein without departing from the scope of the invention as defined in the appended claims.

What is claimed is:

1. A method of modifying the curvature of a patient's live cornea comprising the steps of
separating an internal area of the live cornea into first and second opposed internal surfaces, the first internal surface facing in a posterior direction of the live cornea and the second internal surface facing in an anterior direction of the live cornea,
directing a laser beam onto at least one of the first and second internal surfaces in a predetermined pattern to incrementally ablate, and therefore incrementally remove, three-dimensional portions sequentially thereof, and
recombining the first and second internal surfaces,
the separating, directing and recombining steps taking place without freezing the cornea.

2. A method of modifying the curvature of a patient's live cornea having an exterior surface, comprising the steps of
forming a relatively small opening in the exterior surface of the live cornea,
creating a cavity in and surrounded by the live cornea by separating an internal area of the live cornea into first and second opposed internal surfaces, the cavity being defined by an open end formed by the opening in the exterior surface and by the first and second internal surfaces, the first internal surface of the cavity facing in a posterior direction of the live cornea and the second internal surface of the cavity facing in an anterior direction of the live cornea,
inserting a portion of a tool through the opening into the cavity, said tool being a cutting device inserted between the first and second internal surfaces,
incrementally and completely removing three-dimensional portions of the live cornea sequentially from at least one of the first and second internal surfaces in a predetermined pattern via the tool, and
recombining the first and second internal surfaces,
the creating, separating, removing and recombining steps taking place without freezing the cornea, and
the removing step comprising the step of cutting the internal surfaces without coagulating and without burning the internal surfaces.

3. A method according to claim 2, wherein
the tool used in the cutting step is a rotating drill.

4. A method according to claim 2, wherein
the cavity is ablated to remove a substantially disc-shaped portion of the cornea.

5. A method according to claim 4, wherein
the pocket being ablated is located substantially at the center of the cornea.

6. A method according to claim 2, wherein the creating step comprises
creating additional cavities in and surrounded by the live cornea by separating internal areas of the live cornea, the cavity and the additional cavities being shaped as intrastromal tunnels for receiving the tool, and
repeating the inserting, removing and recombining steps for each of additional cavities formed in the live cornea to modify the curvature of the live cornea.

7. A method according to claim 6, wherein
the tunnel shaped cavities extend substantially radially towards the center of the cornea.

8. A method of modifying the curvature of a patient's live cornea having an exterior surface comprising the steps of
forming a relatively small opening in the exterior surface of the live cornea,
separating an internal area of the live cornea into first and second opposed internal surfaces via the opening, the first internal surface facing in a posterior direction of the live cornea and the second internal surface facing in an anterior direction of the live cornea,
inserting a portion of a laser beam-emitting cable between the first and second internal surfaces,
directing a laser beam from the laser beam-emitting cable onto at least one of the first and second internal surfaces in a predetermined pattern to coagulate a three-dimensional portion thereof to modify the curvature of the cornea, and
recombining the first and second internal surfaces,
the separating, directing and recombining steps taking place without freezing the cornea.

9. The method according to claim 8, wherein the separating step comprises the step of cutting at least one incision into the live cornea to create at least one intrastromal tunnel for receiving the laser beam.

10. The method according to claim 9, wherein the cutting step comprises the step of
cutting a plurality of the incisions into the live cornea to create a plurality of the intrastromal tunnels for receiving the laser beam.

11. The method according to claim 10, wherein
the incisions extend substantially radially towards the center of the cornea.

12. A method of modifying the curvature of a patient's live cornea having an exterior surface comprising the steps of
forming a relatively small opening in the exterior surface of the live cornea,
separating an internal area of the live cornea into first and second opposed internal surfaces via the opening without completely separating the first internal surface from the live cornea, the first internal surface facing in a posterior direction of the live cornea and the second internal surface facing in an anterior direction of the live cornea,
inserting a portion of a laser beam-emitting cable between the first and second internal surfaces,
directing a laser beam from the laser beam-emitting cable onto at least one of the first and second internal surfaces in a predetermined pattern to reduce the thickness of the cornea along these surfaces, and
recombining the first and second internal surfaces.

13. The method according to claim 12, wherein the directing step comprises the step of
ablating at least one of the first and second internal surfaces with the laser beam to decrease the curvature of the cornea.

14. The method according to claim 12, wherein
the separating step comprises the step of cutting a centrally located internal pocket; and
the directing step comprises the step of ablating the pocket to remove a substantially disc-shaped portion of the cornea.

15. The method according to claim 12, wherein
the separating step comprises the step of cutting a plurality of incisions into the live cornea to form a plurality of intrastromal tunnels, and
the directing step comprises the step of ablating each of the tunnels.

16. The method according to claim 15, wherein
the tunnels extend substantially radially inwardly towards the center of the cornea.

17. The method according to claim 12, wherein the directing step comprises the step of
coagulating at least one of the first and second internal surfaces with the laser beam to increase the curvature of the cornea.

18. The method according to claim 17, wherein
the separating step comprises the steps of cutting a plurality of incisions into the live cornea to create a plurality of intrastromal tunnels with the first and second internal surfaces being formed in each of the tunnels, and
the coagulating step comprises the step of coagulating at least one of the first and second internal surfaces of each of the tunnels.

19. The method according to claim 18, wherein
the tunnels extend substantially radially towards the center of the cornea.

20. The method according to claim 19, wherein
each of the tunnels are coagulated at a point, the points of coagulation oriented in a substantially circular array.

21. A method of modifying the curvature of a patient's live cornea having an exterior surface, comprising the steps of
forming a relatively small opening in the exterior surface of the live cornea,
creating a cavity in and surrounded by the live cornea by separating an internal area of the live cornea into first and second opposed internal surfaces, the cavity being defined by an open end formed by the opening in the exterior surface and by the first and second opposed internal surfaces the first internal surface of the cavity facing in a posterior direction of the live cornea and the second internal surface of the cavity facing in an anterior direction of the live cornea,
inserting a portion of a tool through the opening into the cavity,
incrementally and completely removing three-dimensional portions of the live cornea sequentially from at least one of the first and second internal surfaces in a predetermined pattern via the tool, and
recombining the first and second internal surfaces,
the creating, separating, removing and recombining steps taking place without freezing the cornea, and
the removing step comprising the step of subjecting the internal surfaces to laser energy via the tool.

22. A method of modifying the curvature of a patient's live cornea having an exterior surface comprising the steps of
forming a relatively small opening in the exterior surface of the live cornea,
separating an internal area of the live cornea into first and second opposed internal surfaces via the opening, the first internal surface facing in a posterior direction of the live cornea and the second internal surface facing in an anterior direction of the live cornea,
inserting a portion of a laser beam-emitting cable between the first and second internal surfaces,
directing a laser beam from the laser beam-emitting cable onto at least one of the first and second internal surfaces in a predetermined pattern to incrementally ablate, and therefore incrementally and completely remove, three-dimensional portions sequentially thereof, and
recombining the first and second internal surfaces,
the separating, directing and recombining steps taking place without freezing the cornea.

23. A method according to claim 22, wherein the separating step comprises the step of
cutting an incision into the live cornea and creating an intrastromal pocket in the cornea for receiving the laser beam.

24. A method according to claim 23, wherein the directing step comprises the step of
ablating only one of the first and second internal surfaces of the pocket with the laser beam.

25. A method according to claim 23, wherein the directing step comprises the step of
ablating both the first and second internal surfaces of the pocket with the laser beam.

26. A method according to claim 23, wherein the pocket is ablated to remove a substantially disc-shaped portion of the cornea.

27. A method according to claim 26, wherein the pocket being ablated is located substantially at the center of the cornea.

28. A method according to claim 27, wherein the separating step comprises the step of cutting a plurality of incisions into the live cornea to create a plurality of intrastromal tunnels in the cornea for receiving the laser beam.

29. A method according to claim 28, wherein the tunnels extend substantially radially towards the center of the cornea.

30. A method according to claim 28, wherein the directing step comprises the step of ablating only one of the first and second internal surfaces of each of the tunnels with the laser beam.

31. A method according to claim 7, wherein the directing step comprises the step of ablating both of the first and second internal surfaces of each of the tunnels with the laser beam.

* * * * *